(12) United States Patent
Overmyer

(10) Patent No.: US 11,864,954 B2
(45) Date of Patent: *Jan. 9, 2024

(54) MANUAL KNIFE BAILOUT MONITORING USING INDUCTIVE COUPLING

(71) Applicant: Cilag GmbH International, Zug (CH)

(72) Inventor: Mark D. Overmyer, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 47 days.

This patent is subject to a terminal disclaimer.

(21) Appl. No.: 17/540,478

(22) Filed: Dec. 2, 2021

(65) Prior Publication Data
US 2022/0087769 A1   Mar. 24, 2022

Related U.S. Application Data

(63) Continuation of application No. 16/547,270, filed on Aug. 21, 2019, now Pat. No. 11,202,686.

(51) Int. Cl.
*A61B 17/072* (2006.01)
*A61B 90/00* (2016.01)
(Continued)

(52) U.S. Cl.
CPC .......... *A61B 90/06* (2016.02); *A61B 17/072* (2013.01); *A61B 17/07207* (2013.01); *A61B 34/30* (2016.02); *A61B 34/37* (2016.02); *A61B 34/76* (2016.02); *A61B 17/068* (2013.01); *A61B 2017/00017* (2013.01);
(Continued)

(58) Field of Classification Search
CPC ............... A61B 17/068; A61B 17/072; A61B 17/07207; A61B 17/115; A61B 2017/00017; A61B 2017/00022; A61B 2017/00473; A61B 2017/00477; A61B 2017/00398; A61B 2017/00734; A61B 2017/00199; A61B 2017/07214; A61B 2017/07228; A61B 2017/07271; A61B 2017/07285; A61B 2017/2927; A61B 2017/2929; A61B 2017/2943; A61B 34/20; A61B 34/30; A61B 34/37; A61B 34/76; A61B 90/06; A61B 2090/0808; A61B 2090/0811; A61B 2090/064; A61B 18/1445
USPC .. 227/19, 175.1, 175.2, 176.1, 180.1, 175.3; 606/1, 41, 139, 153, 205, 219
See application file for complete search history.

(56) References Cited

U.S. PATENT DOCUMENTS 5,269,794 A * 12/1993 Rexroth ........... A61B 17/32002
606/167
6,783,524 B2 * 8/2004 Anderson ............. A61B 34/37
606/1

(Continued)

*Primary Examiner* — Scott A Smith
(74) *Attorney, Agent, or Firm* — Vorys, Sater, Seymour, and Pease LLP

(57) ABSTRACT

A robotic surgical tool includes a tool driver, and a drive housing inductively coupled to the tool driver when mounted to the tool driver and generating a magnetic field, the drive housing including one or more component parts made of or including a magnetically responsive material. A computer system is programmed to process an intensity of the magnetic field and a field distortion caused by the one or more component parts, and further programmed to generate a notification when the field distortion changes.

19 Claims, 7 Drawing Sheets

(51) Int. Cl.
    *A61B 34/37*    (2016.01)
    *A61B 34/00*    (2016.01)
    *A61B 34/30*    (2016.01)
    *A61B 17/00*    (2006.01)
    *A61B 17/068*   (2006.01)
    *A61B 17/29*    (2006.01)

(52) U.S. Cl.
    CPC ........... *A61B 2017/00123* (2013.01); *A61B 2017/00199* (2013.01); *A61B 2017/00398* (2013.01); *A61B 2017/00477* (2013.01); *A61B 2017/07214* (2013.01); *A61B 2017/07285* (2013.01); *A61B 2017/2927* (2013.01); *A61B 2090/0811* (2016.02); *A61B 2562/0223* (2013.01)

(56) References Cited

U.S. PATENT DOCUMENTS

| | | | | |
|---|---|---|---|---|
| 7,524,320 B2* | 4/2009 | Tierney | | A61B 34/30 606/1 |
| 8,461,744 B2* | 6/2013 | Wiener | | A61B 18/1445 606/171 |
| 11,202,686 B2* | 12/2021 | Overmyer | | A61B 17/072 |
| 2006/0278680 A1* | 12/2006 | Viola | | A61B 17/072 227/176.1 |
| 2009/0101692 A1* | 4/2009 | Whitman | | A61B 17/07207 227/175.1 |
| 2010/0264193 A1* | 10/2010 | Huang | | A61B 17/068 227/176.1 |
| 2011/0017801 A1* | 1/2011 | Zemlok | | A61B 17/07207 227/175.1 |
| 2011/0290855 A1* | 12/2011 | Moore | | A61B 34/30 227/176.1 |
| 2012/0132450 A1* | 5/2012 | Timm | | A61B 17/072 29/700 |
| 2012/0298719 A1* | 11/2012 | Shelton, IV | | A61B 34/30 227/176.1 |
| 2013/0325034 A1* | 12/2013 | Schena | | A61B 90/98 606/130 |
| 2014/0005718 A1* | 1/2014 | Shelton, IV | | A61B 34/30 606/205 |
| 2015/0209059 A1* | 7/2015 | Trees | | A61B 18/1445 606/205 |
| 2015/0272572 A1* | 10/2015 | Overmyer | | A61B 90/98 227/177.1 |
| 2015/0272575 A1* | 10/2015 | Leimbach | | A61B 90/96 227/175.3 |
| 2017/0196637 A1* | 7/2017 | Shelton, IV | | A61B 34/37 |
| 2017/0202609 A1* | 7/2017 | Shelton, IV | | A61B 18/1445 |

* cited by examiner

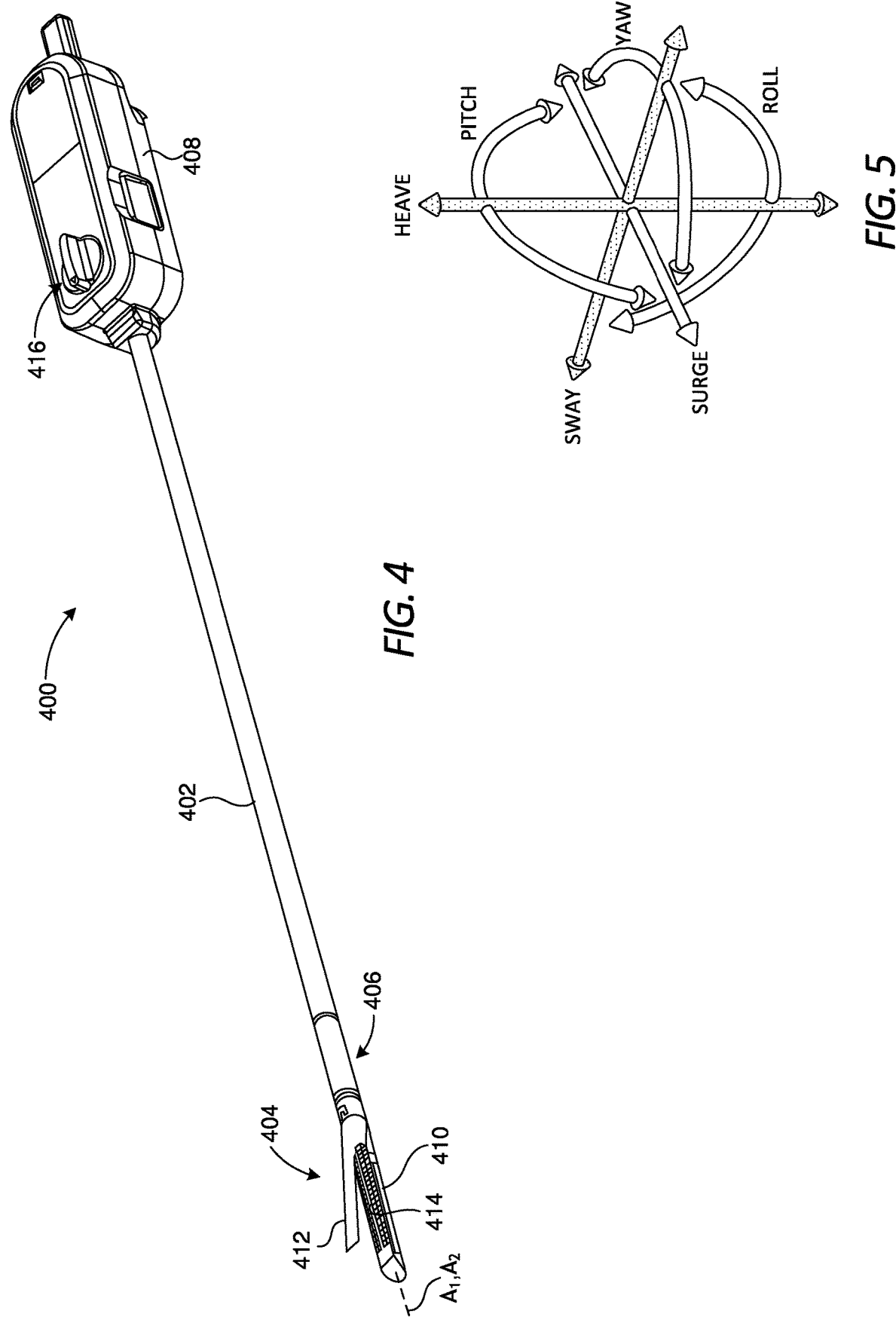

MANUAL KNIFE BAILOUT MONITORING USING INDUCTIVE COUPLING

CROSS-REFERENCE TO RELATED APPLICATIONS

This application is a continuation of U.S. patent application Ser. No. 15/547,270, filed on Aug. 21, 2019, now U.S. Pat. No. 11,202,686. The entire contents of all of the foregoing applications are incorporated by reference herein.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, and needle holders, and are similar to those used in conventional (open) surgery except that the end effector of each tool is separated from its handle by an approximately 12-inch long, shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Surgical staplers are one type of end effector capable of cutting and simultaneously stapling (fastening) transected tissue. Alternately referred to as an "endocutter," the surgical stapler includes opposing jaws capable of opening and closing to grasp and release tissue. Once tissue is grasped or clamped between the opposing jaws, the end effector may be "fired" to advance a cutting element or knife distally to transect grasped tissue. As the cutting element advances, staples contained within the end effector are progressively deployed to seal opposing sides of the transected tissue.

Some surgical staplers include a knife bailout mechanism or system that allows the user to manually retract the knife in the event of an emergency, such as a loss of power. It may be desirable to communicate the status of a manual knife bailout system to the user, but including various sensors in the end effector to sense whether the knife is being manually bailed out may not be feasible.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 4 is an isometric side view of an example surgical tool that may incorporate some or all of the principles of the present disclosure.

FIG. 5 illustrates potential degrees of freedom in which the wrist of FIG. 4 may be able to articulate (pivot).

DETAILED DESCRIPTION

The present disclosure is related to robotic surgical instruments and, more particularly, to systems and methods of sensing when a manual knife bailout system for a robotic surgical tool has been activated or is about to be activated.

Embodiments discussed herein describe a robotic surgical tool that has a tool driver in communication with a computer system, and a drive housing mountable to the tool driver and including one or more component parts made of or including a magnetically responsive material. A first inductor coil may be included on the tool driver and configured to generate a magnetic field, and a second inductor coil may be included on the drive housing and configured to measure an intensity of the magnetic field and a field distortion caused by the one or more component parts. When a change in the field distortion is measured, that may be an indication of movement of the one or more component parts. In some embodiments, the one or more component parts form part of a manual knife bailout system, and measuring the change in the field distortion may provide an indication that the manual knife bailout system has been activated or is about to be activated. When the change in field distortion is measures, the computer system may provide a notification to a user (e.g., a surgeon, a scrub nurse, etc.) of the status change.

Figure 1:
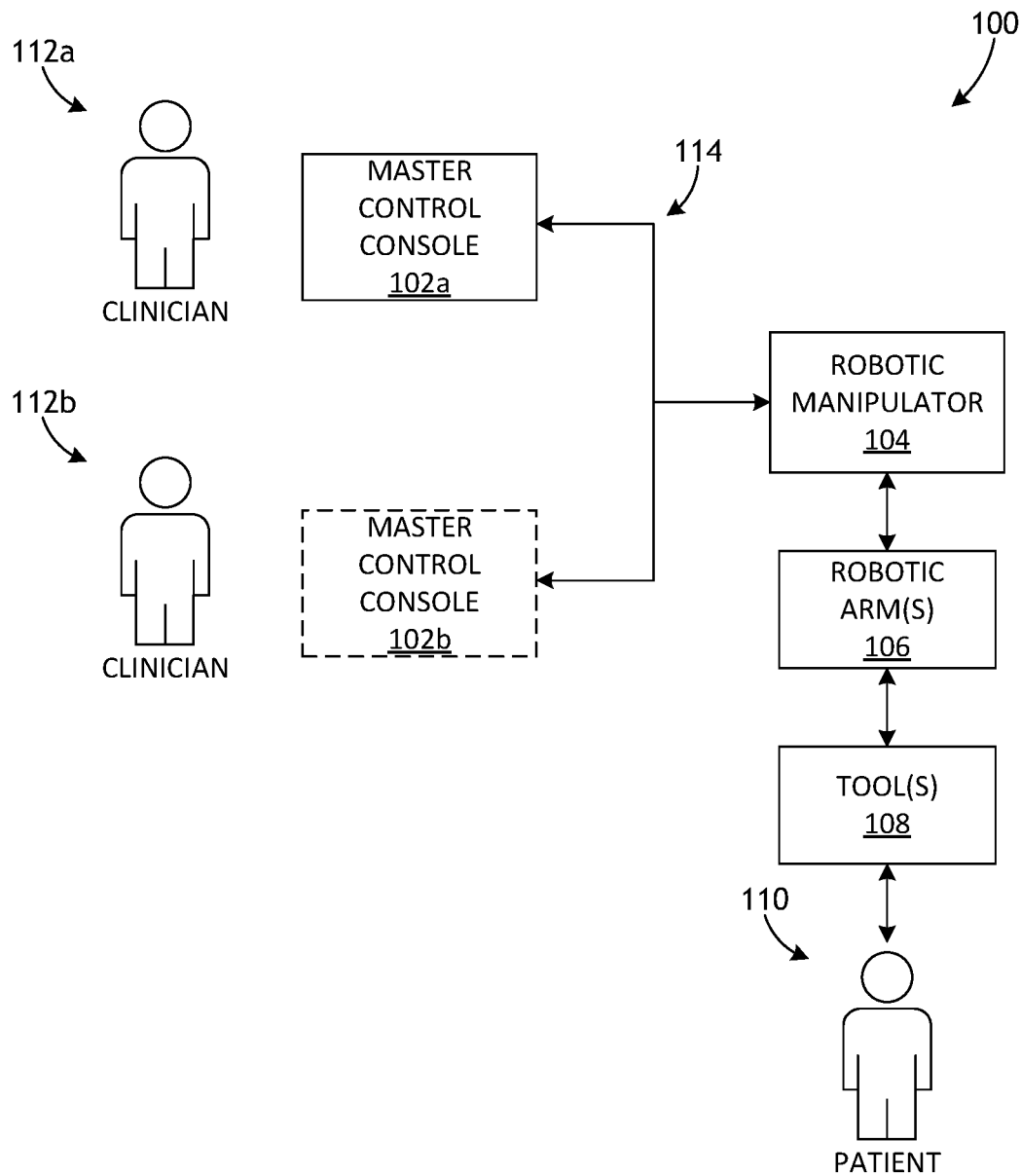
FIG. 1 is a block diagram of an example robotic surgical system that may incorporate some or all of the principles of the present disclosure.
Figure 3:
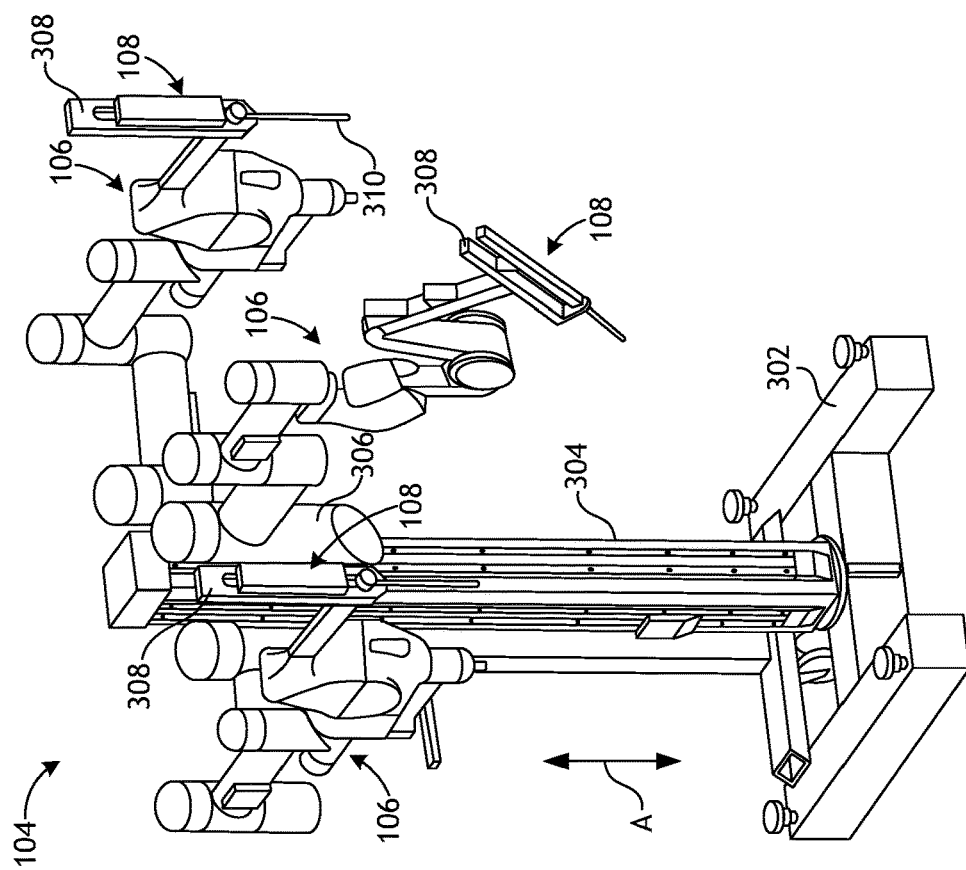
FIG. 3 depicts one example of the robotic manipulator of FIG. 1, according to one or more embodiments.
Figure 2:
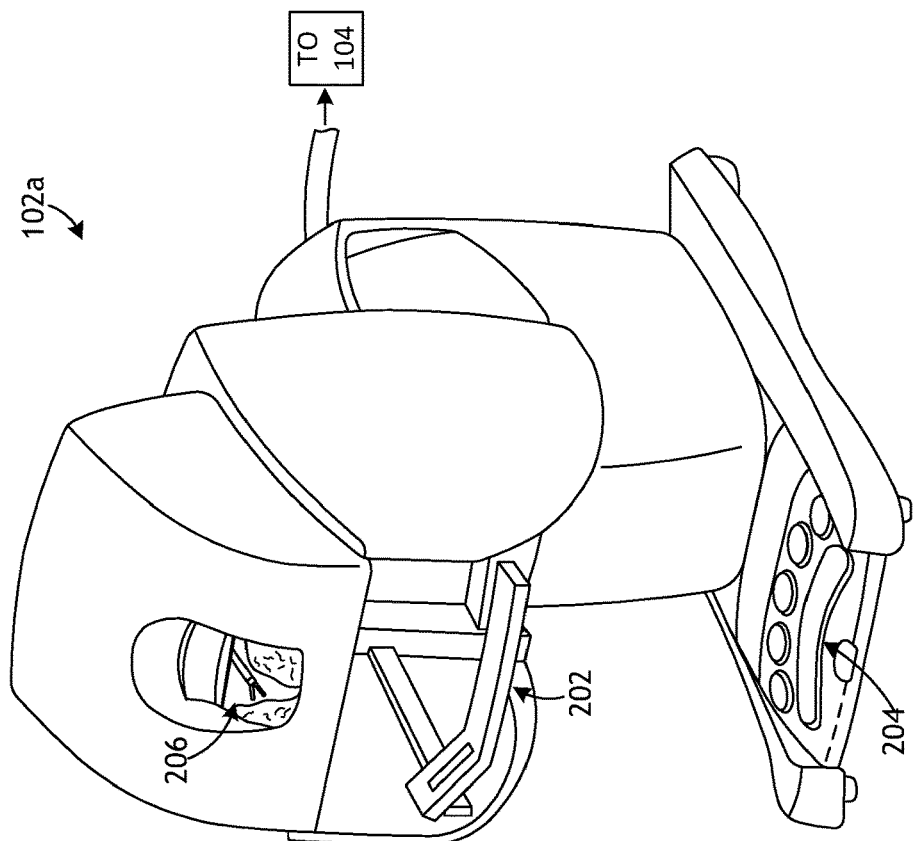
FIG. 2 is an example embodiment of one of the master control consoles of FIG. 1.

FIGS. 1-3 illustrate the structure and operation of an example robotic surgical system and associated components thereof. While applicable to robotic surgical systems, it is noted that the principles of the present disclosure may alternatively be applied to non-robotic surgical systems, without departing from the scope of the disclosure.

FIG. 1 is a block diagram of an example robotic surgical system 100 that may incorporate some or all of the principles of the present disclosure. As illustrated, the system 100 can include at least one master control console 102a and at least one robotic manipulator 104. The robotic manipulator 104 may be mechanically and/or electrically coupled to or otherwise include one or more robotic arms 106. In some embodiments, the robotic manipulator 104 may be mounted to a transport cart (alternately referred to as an "arm cart") that enables mobility of the robotic manipulator 104 and the associated robotic arms 106. Each robotic arm 106 may include and otherwise provide a tool driver where one or more surgical instruments or tools 108 may be mounted for performing various surgical tasks on a patient 110. Operation of the robotic arms 106, the corresponding tool drivers, and the associated tools 108 may be directed by a clinician 112a (e.g., a surgeon) from the master control console 102a.

In some embodiments, a second master control console 102b (shown in dashed lines) operated by a second clinician 112b may also help direct operation of the robotic arms 106 and the tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators having additional robotic arms may be utilized during surgery on a patient 110, and these additional robotic arms may be controlled by one or more of the master control consoles 102a,b.

The robotic manipulator 104 and the master control consoles 102a,b may communicate with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Accordingly, the clinicians 112a,b may be able to remotely control operation of the robotic arms 106 via the communications link 114, thus enabling the clinicians 112a,b to operate on the patient 110 remotely.

FIG. 2 is one example embodiment of the master control console 102a that may be used to control operation of the robotic manipulator 104 of FIG. 1. As illustrated, the master control console 102a can include a support 202 on which the clinician 112a,b (FIG. 1) can rest his/her forearms while gripping one or more user input devices (not shown). The user input devices can comprise, for example, physical controllers such as, but not limited to, hand-held actuator modules, a joystick, exoskeletal gloves, a master manipulator, etc., and may be movable in multiple degrees of freedom to control the position and operation of the surgical tool(s) 108 (FIG. 1). The master control console 102a may further include one or more foot pedals 204 engageable by the clinician 112a,b to change the configuration of the surgical system and/or generate additional control signals to control operation of the surgical tool(s) 108.

The user input devices and/or the foot pedals 204 may be manipulated while the clinician 112a,b (FIG. 1) views the procedure via a visual display 206. Images displayed on the visual display 206 may be obtained from an endoscopic camera or "endoscope." In some embodiments, the visual display 206 may include or otherwise incorporate a force feedback meter or "force indicator" that provides the clinician 112a,b with a visual indication of the magnitude of force being assumed by the surgical tool (i.e., a cutting instrument or dynamic clamping member) and in which direction. As will be appreciated, other sensor arrangements may be employed to provide the master control console 102a with an indication of other surgical tool metrics, such as whether a staple cartridge has been loaded into an end effector or whether an anvil has been moved to a closed position prior to firing, for example.

FIG. 3 depicts one example of the robotic manipulator 104 that may be used to operate a plurality of surgical tools 108, according to one or more embodiments. As illustrated, the robotic manipulator 104 may include a base 302 that supports a vertically extending column 304. A plurality of robotic arms 106 (three shown) may be operatively coupled to the column 304 at a carriage 306 that can be selectively adjusted to vary the height of the robotic arms 106 relative to the base 302, as indicated by the arrow A.

The robotic arms 106 may comprise manually articulable linkages, alternately referred to as "set-up joints." In the illustrated embodiment, a surgical tool 108 is mounted to corresponding tool drivers 308 provided on each robotic arm 106. Each tool driver 308 may include one or more drivers or motors used to interact with a corresponding one or more drive inputs of the surgical tools 108, and actuation of the drive inputs causes the associated surgical tool 108 to operate.

One of the surgical tools 108 may comprise an image capture device 310, such as an endoscope, which may include, for example, a laparoscope, an arthroscope, a hysteroscope, or may alternatively include some other imaging modality, such as ultrasound, infrared, fluoroscopy, magnetic resonance imaging, or the like. The image capture device 310 has a viewing end located at the distal end of an elongate shaft, which permits the viewing end to be inserted through an entry port into an internal surgical site of a patient's body. The image capture device 310 may be communicably coupled to the visual display 206 (FIG. 2) and capable of transmitting images in real-time to be displayed on the visual display 206.

The remaining surgical tools may be communicably coupled to the user input devices held by the clinician 112a,b (FIG. 1) at the master control console 102a (FIG. 2). Movement of the robotic arms 106 and associated surgical tools 108 may be controlled by the clinician 112a,b manipulating the user input devices. As described in more detail below, the surgical tools 108 may include or otherwise incorporate an end effector mounted on a corresponding articulable wrist pivotally mounted on a distal end of an associated elongate shaft. The elongate shaft permits the end effector to be inserted through entry ports into the internal surgical site of a patient's body, and the user input devices also control movement (actuation) of the end effector.

In use, the robotic manipulator 104 is positioned close to a patient requiring surgery and is then normally caused to remain stationary until a surgical procedure to be performed has been completed. The robotic manipulator 104 typically has wheels or casters to render it mobile. The lateral and vertical positioning of the robotic arms 106 may be set by the clinician 112a,b (FIG. 1) to facilitate passing the elongate shafts of the surgical tools 108 and the image capture device 310 through the entry ports to desired positions relative to the surgical site. When the surgical tools 108 and image capture device 310 are so positioned, the robotic arms 106 and carriage 306 can be locked in position.

FIG. 4 is an isometric side view of an example surgical tool 400 that may incorporate some or all of the principles of the present disclosure. The surgical tool 400 may be the same as or similar to at least one of the surgical tools 108 of FIGS. 1 and 3 and, therefore, may be used in conjunction with a robotic surgical system, such as the robotic surgical system 100 of FIG. 1. As illustrated, the surgical tool 400 includes an elongated shaft 402, an end effector 404, an articulable wrist 406 (alternately referred to as a "wrist joint") that couples the end effector 404 to the distal end of the shaft 402, and a drive housing 408 coupled to the proximal end of the shaft 402. In applications where the surgical tool 400 is used in conjunction with a robotic surgical system, the drive housing 408 can include coupling features that releasably couple the surgical tool 400 to the robotic surgical system. The principles of the present disclosure, however, are equally applicable to surgical tools that are non-robotic and otherwise capable of manual manipulation.

The terms "proximal" and "distal" are defined herein relative to a robotic surgical system having an interface configured to mechanically and electrically couple the surgical tool 400 (e.g., the drive housing 408) to a robotic manipulator. The term "proximal" refers to the position of an element closer to the robotic manipulator and the term "distal" refers to the position of an element closer to the end effector 404 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 400 can have any of a variety of configurations capable of performing one or more surgical functions. In the illustrated embodiment, the end effector 404 comprises a surgical stapler, alternately referred to as an "endocutter," configured to cut and staple (fasten) tissue. As illustrated, the end effector 404 includes opposing jaws 410, 412 configured to move (articulate) between open and closed positions. The opposing jaws 410, 412, however, may alternately form part of other types of end effectors that include jaws such as, but not limited to, tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. One or both of the jaws 410, 412 may be configured to pivot to actuate the end effector 404 between the open and closed positions. In the illustrated example, the second jaw 412 is rotatable (pivotable) relative to the first jaw 410 to move between an open, unclamped position and a closed, clamped position. In other embodiments, however, the first jaw 410 may move (rotate) relative to the second jaw 412, without departing from the scope of the disclosure.

In the illustrated example, the first jaw 410 may be characterized or otherwise referred to as a "cartridge" jaw, and the second jaw 412 may be characterized or otherwise referred to as an "anvil" jaw. The first jaw 410 may include a frame that houses or supports a staple cartridge, and the second jaw 412 is pivotally supported relative to the first jaw 410 and defines a surface that operates as an anvil to deform staples ejected from the staple cartridge during operation.

The wrist 406 enables the end effector 404 to articulate (pivot) relative to the shaft 402 and thereby position the end effector 404 at desired orientations and locations relative to a surgical site. FIG. 5 illustrates the potential degrees of freedom in which the wrist 406 may be able to articulate (pivot). The wrist 406 can have any of a variety of configurations. In general, the wrist 406 comprises a joint configured to allow pivoting movement of the end effector 404 relative to the shaft 402. The degrees of freedom of the wrist 406 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 404) with respect to a given reference Cartesian frame. As depicted in FIG. 5, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 406 (e.g., X-axis), yaw movement about a second axis of the wrist 406 (e.g., Y-axis), and combinations thereof to allow for 360° rotational movement of the end effector 404 about the wrist 406. In other applications, the pivoting motion can be limited to movement in a single plane, e.g., only pitch movement about the first axis of the wrist 406 or only yaw movement about the second axis of the wrist 406, such that the end effector 404 moves only in a single plane.

Referring again to FIG. 4, the surgical tool 400 may incorporate or include an actuation system designed to facilitate articulation of the wrist 406 and actuation (operation) of the end effector 404 (e.g., clamping, firing, rotation, articulation, energy delivery, etc.). The actuation system may include a plurality of drive members or the like (obscured in FIG. 4) that extend from the drive housing 408 to the wrist 406, and selective actuation of these drive members causes the end effector 404 to articulate (pivot) relative to the shaft 402 at the wrist 406. The end effector 404 is depicted in FIG. 4 in the unarticulated position where a longitudinal axis $A_2$ of the end effector 404 is substantially aligned with the longitudinal axis $A_1$ of the shaft 402, such that the end effector 404 is at a substantially zero angle relative to the shaft 402. In the articulated position, the longitudinal axes $A_1$, $A_2$ would be angularly offset from each other such that the end effector 404 is at a non-zero angle relative to the shaft 402.

Other drive members may extend to the end effector 404, and selective actuation of those drive members may cause the end effector 404 to actuate (operate). Actuating the end effector 404 may include closing and/or opening the second jaw 412 relative to the first jaw 410 (or vice versa), thereby enabling the end effector 404 to grasp (clamp) onto tissue. Once tissue is grasped or clamped between the opposing jaws 410, 412, actuating the end effector 404 may further include "firing" the end effector 404, which may refer to causing a cutting element or knife (not visible) to advance distally within a slot 414 defined in the second jaw 410. As it moves distally, the cutting element may transect any tissue grasped between the opposing jaws 410, 412. Moreover, as the cutting element advances distally, a plurality of staples contained within the staple cartridge (e.g., housed within the first jaw 410) may be urged (cammed) into deforming contact with corresponding anvil surfaces (e.g., pockets) provided on the second jaw 412. The deployed staples may form multiple rows of staples that seal opposing sides of the transected tissue.

In some applications, the surgical tool 400 may also be configured to apply energy to tissue, such as radio frequency (RF) energy. In such cases, actuating the end effector 404 may further include applying energy to tissue grasped or clamped between two opposing jaws to cauterize or seal the captured tissue, following which the tissue may be transected.

The surgical tool 400 may further include a manual jaw bailout system that enables a user to manually open and close the jaws 410, 412. In the illustrated embodiment, the manual jaw bailout system may include a bailout tool 416 accessible to a user on the exterior of the drive housing 408. The bailout tool 416 may be operatively coupled to various gears and/or drive members located within the drive housing 408 to allow a clinician to manually open and close the jaws 410, 412. By rotating the bailout tool 416 in either angular direction, a clinician may be able to fully clamp and fully unclamp the jaws 410, 412. The bailout tool 416 may be particularly useful to a clinician when the surgical tool 400 is detached from a surgical robot, since having the capability to open and close the jaws 410, 412 may eliminate the need to place inadvertent stress on internal drive members or components. In the event that a clinician desires to manually open the jaws 410, 412 when the surgical tool 400 is still attached to a surgical robot, the clinician can rotate the bailout tool 416 in an attempt to open the end effector 404.

Figure 6:
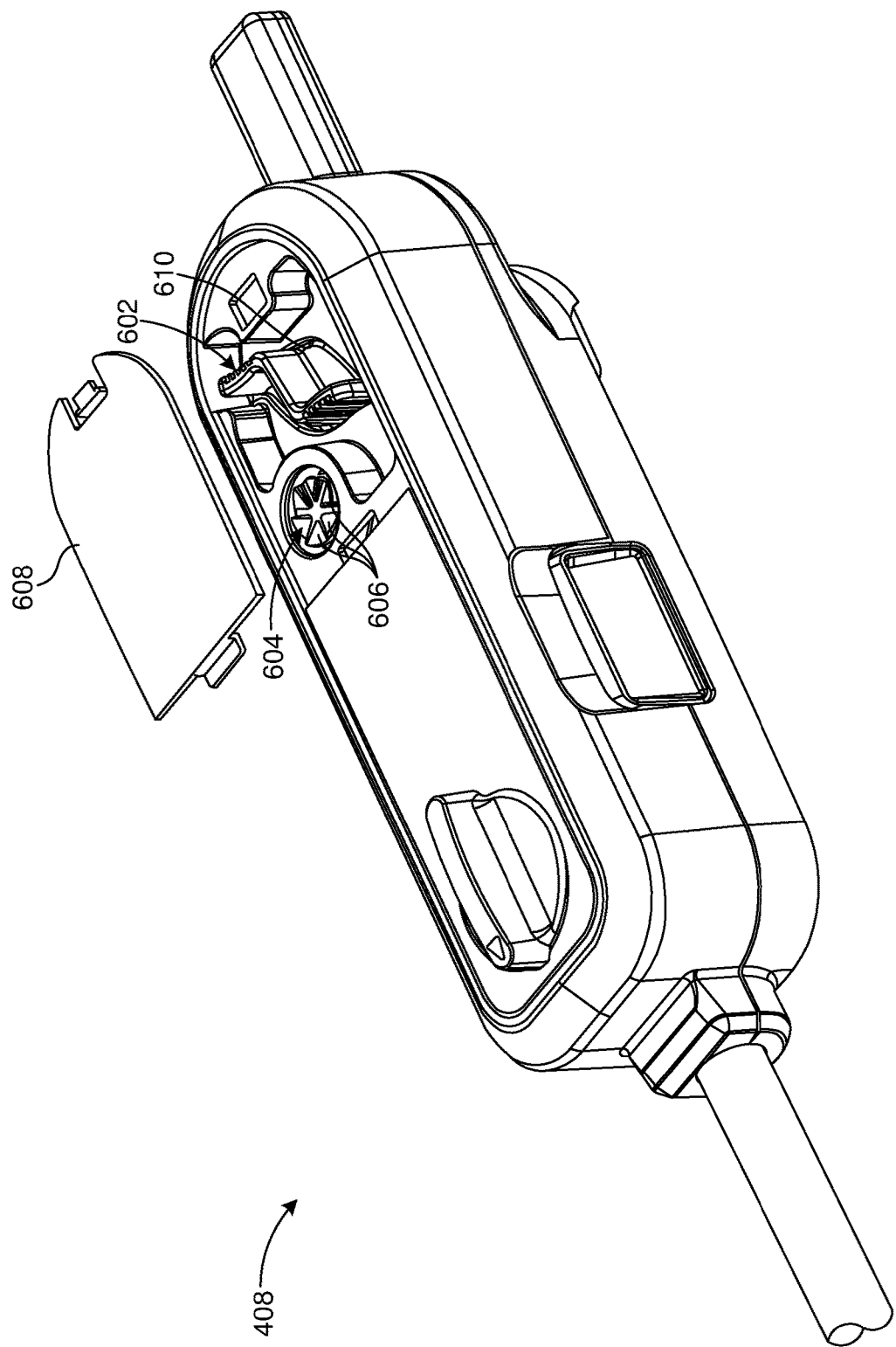
FIG. 6 is an enlarged isometric view of the drive housing of FIG. 4.

FIG. 6 is an enlarged isometric view of the drive housing 408. In some embodiments, the surgical tool 400 may include a manual knife bailout system that allows a user to manually retract the knife (cutting element) at the end effector 404 (FIG. 4). The manual knife bailout system includes various component parts, such as a bailout tool 602 accessible to a user and configured to mate with a bailout cap 604 to cause knife retraction. The bailout cap 604 may include or otherwise provide one or more surface features 606 configured to interact with corresponding engagement features (not shown) provided on the bottom of the bailout tool 602. Each surface feature 606 may be ramped in one angular direction and terminate at a raised shoulder. The engagement features of the bailout tool 602 may be configured to engage the raised shoulders of the surface features 606 when the bailout tool 602 is rotated in a first direction (e.g., counter-clockwise), thus transmitting torque from the bailout tool 602 to the bailout cap 604. In contrast, when the bailout tool 602 is rotated in a second direction (e.g., clockwise), the engagement features may traverse (ride up) and ratchet over the surface features 606. Accordingly, the bailout cap 604 may operate as a unidirectional transfer member.

In example use of the manual knife bailout system, a user rotating the bailout tool 602 in the first direction (e.g., counter-clockwise) will drive the bailout cap 604 in the same direction and thereby cause the gears of the firing system to rotate, which will rotate the firing pinion and thereby retract a firing rack so that an interconnected firing rod (not shown) can retract the knife at the end effector 404 (FIG. 4). When the bailout tool 602 is rotated in the second direction (e.g., clockwise), however, the bailout tool 602 will ratchet over the surface features 606 and otherwise rotate relative to the bailout cap 604, thus not affecting the position of the firing rod or the knife.

In the illustrated embodiment, the bailout tool 602 comprises a separate component part stored within the drive housing 408 and is accessible to the user by first removing a bailout panel 608 from the body of the drive housing 408. As illustrated, the bailout tool 602 may be seated within a pocket 610 and the user may remove the bailout tool 602 from the pocket 610 and mate it with the bailout cap 604 to manually retract the knife. In other embodiments, however, the bailout tool 602 may be located on the exterior of the drive housing 408 and extend through the bailout panel 608 of the drive housing 408 to be operatively coupled to the bailout cap 604. In yet other embodiments, the bailout tool 602 may be attached to or form part of the bottom (underside) of the bailout panel 608. In such embodiments, the clinician may remove the bailout panel 608 and align the interconnected bailout tool 602 with the bailout cap 604, thus converting the removable bailout panel 608 into a type of wrench.

Figure 7:
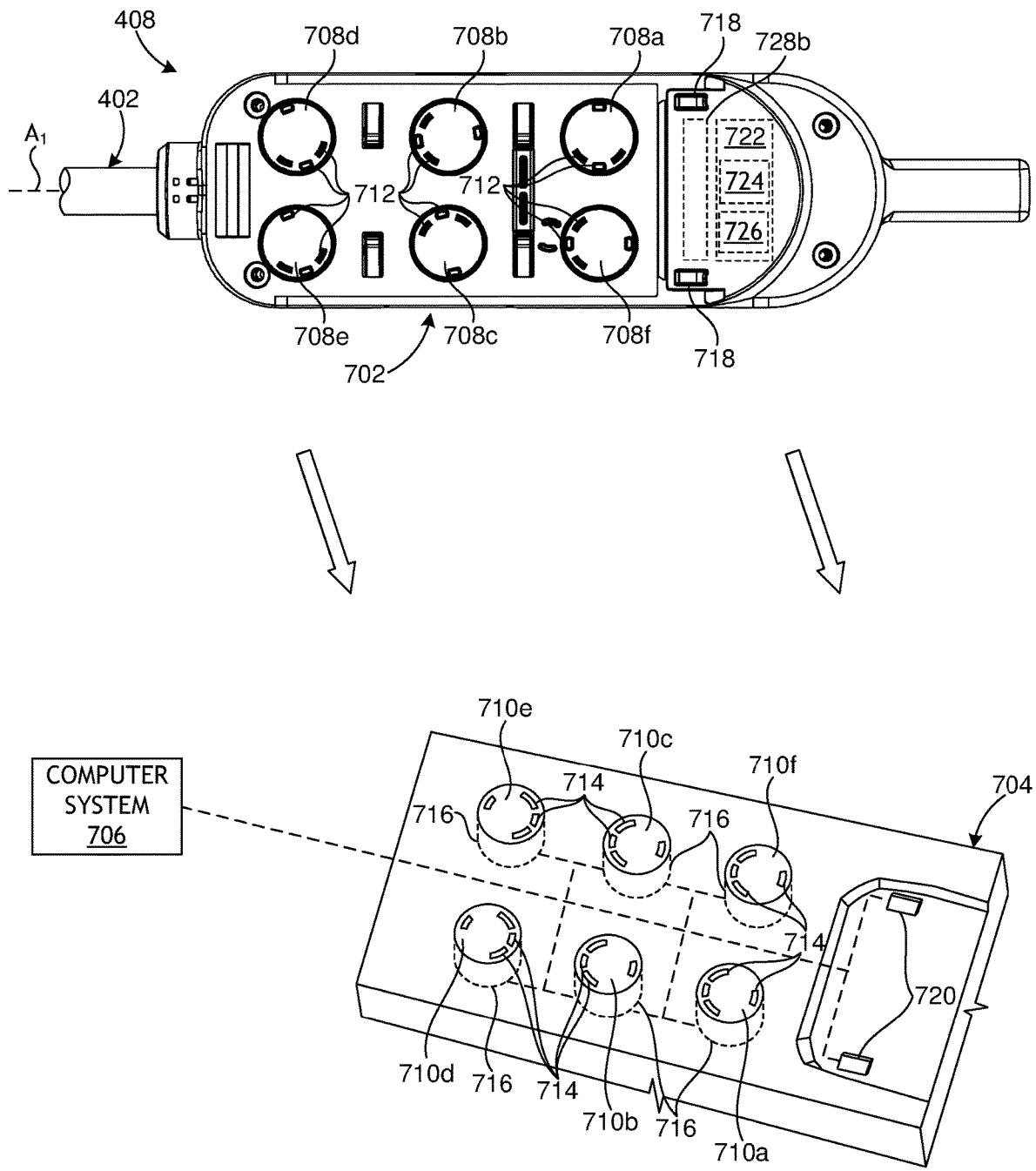
FIG. 7 is a bottom view of the drive housing of FIG. 4, according to one or more embodiments.

FIG. 7 is a bottom view of the drive housing 408, according to one or more embodiments. As illustrated, the drive housing 408 may include a tool mounting portion 702 used to operatively couple the drive housing 408 to a tool driver 704. The tool driver 704 may be the same as or similar to the tool drivers 308 of FIG. 3, and may thus be operable in conjunction with the robotic manipulator 104 of FIGS. 1 and 3. Mounting the drive housing 408 to the tool driver 704 places the drive housing 408 in communication with a computer system 706, which may communicate with or otherwise form part of the master controllers 102a,b (FIG. 1). The computer system 706 monitors and directs operation of the drive housing 408 via operation of the tool driver 704, thus enabling a user (e.g., the clinicians 112a,b of FIG. 1) to control operation of the drive housing 408 by working through the master controller 102a,b.

The tool mounting portion 702 includes and otherwise provides an interface that mechanically, magnetically, and/or electrically couples the drive housing 408 to the tool driver 704. In at least one embodiment, the tool mounting portion 702 couples the drive housing 408 to the tool driver 704 via a sterile barrier (not shown). As illustrated, the interface can include and support a plurality of inputs, shown as drive inputs 708a, 708b, 708c, 708d, 708e, and 708f. Each drive input 708a-f may comprise a rotatable disc configured to align (mate) with and couple to a corresponding driver 710a, 710b, 710c, 710d, 710e, and 710f of the tool driver 704. Each drive input 708a-f and corresponding driver 710a-f provide or define one or more matable surface features 712 and 714, respectively, configured to facilitate mating engagement between the opposing surface features 712, 714 such that movement (rotation) of a given driver 710a-f correspondingly moves (rotates) the associated drive input 708a-f.

Each driver 710a-f may include or otherwise comprise a motor 716 configured to actuate the corresponding driver 710a-f, and actuation of a given driver 710a-f correspondingly causes actuation of the mated drive input 708a-f, which facilitates operation of the mechanics of the drive housing 408. More specifically, actuation of a given motor 716 may cause rotational movement of the corresponding driver 710a-f, which, in turn, rotates the associated drive input 708a-f operatively coupled thereto. Each motor 716 may be in communication with the computer system 706 and, based on input signals provided by a user (e.g., a surgeon), the computer system 706 may selectively cause any of the motors 716 to actuate and thereby drive the corresponding driver 710a-f to operate the mechanical systems of the drive housing 408.

In some embodiments, actuation of the first drive input 708a via the first driver 710a may control rotation of the shaft 402 about its longitudinal axis $A_1$. Depending on the rotational direction of the first drive input 708a, the shaft 402 can be rotated clockwise or counter-clockwise, thus correspondingly rotating the end effector 404 (FIG. 4) in the same direction. Actuation of the second and third drive inputs 708b,c via the second and third drivers 710a,b, respectively, may control articulation of the end effector 404 at the wrist 406 (FIG. 4). Actuation of the fourth and fifth drive inputs 708d,e via the fourth and fifth drivers 710d,e, respectively, may cause an outer portion of the shaft 402 (referred to herein as a "closure tube") to advance and retract, which closes and opens the jaws 410, 412 (FIG. 4). Lastly, actuation of the sixth drive input 708f via the sixth driver 710f may cause the end effector 404 to fire, which may entail distal deployment of a knife (cutting element) to transect tissue grasped by the jaws 410, 412 and simultaneous deployment of staples contained within the staple cartridge housed within the first jaw 410.

The drive housing 408 may house or otherwise include an internal computer 722 that may include a memory 724 and/or a microprocessor 726. The memory 724 may include one or more databases or libraries that store data relating to the drive housing 408 and, more particularly, to the surgical tool 400 (FIG. 4). In some embodiments, the memory 724 may include non-transitory, computer-readable media such as a read-only memory (ROM), which may be PROM, EPROM, EEPROM, or the like.

Mounting (coupling) the tool mounting portion 702 to the tool driver 704 facilitates communication and power transfer between the tool driver 704 and the drive housing 408. More specifically, mating the drive housing 408 to the tool driver 704 places the internal computer 722 in communication with the computer system 706, which allows the computer system 706 to identify and authenticate the surgical tool 400 (FIG. 4) or otherwise associate the surgical tool 400 with data stored elsewhere in the robotic surgical system. In some embodiments, to facilitate communication and power transfer between the tool mounting portion 702 and the tool driver 704, the tool mounting portion 702 may include one or more electrical connectors 718 (two shown) configured to mate with corresponding electrical connections 720 (two shown) provided by the tool driver 704 to.

Alternately, or in addition thereto, the drive housing 408 can be inductively (or "magnetically) coupled to the tool driver 704 to facilitate wireless communication and power transfer between the two structures. In at least one embodiment, for example, the drive housing 408 may be inductively coupled to the tool driver 704 using a near field communication (NFC) connection or protocol. In other embodiments, however, the drive housing 408 may be inductively coupled to the tool driver 704 via other wireless communication protocols.

In the illustrated embodiment, a first or "transmitting" inductor coil 728a (shown in dashed lines) may be included on the tool driver 704, and a corresponding second or "receiving" inductor coil 728b (shown in dashed lines) may be included on the drive housing 408, such as being arranged on the tool mounting portion 702. The first inductor coil 728a may be communicably coupled to the computer system 706, and the second inductor coil 728b may be communicably coupled to the internal computer 722 of the drive housing 408. Once the first and second inductor coils 728a,b are inductively coupled, data may be transferred between the computer system 706 and the internal computer 722.

The first inductor coil 728a may be operated and powered by the computer system 706 and configured to generate (emit) a magnetic field, which induces an electromotive force (i.e., a voltage or a current) in the adjacent second inductor coil 728b. Based on the changing intensity of the magnetic field, the generated electromotive force can be interpreted by the internal computer 722 to transmit data between the two structures. Moreover, the generated electromotive force may be harvested in the form of electrical power, which may be used to power the circuitry of the internal computer 722.]

According to embodiments of the present disclosure, the inductive coupling between the drive housing 408 and the tool driver 704 may also be used to determine when the manual knife bailout system of the surgical tool 400 (FIG. 4) is activated or about to be activated. More specifically, embodiments of the present disclosure rely on the effect that a magnetically responsive material (e.g., conductive or ferrous materials) can have on the magnetic field generated by the inductive coupling. One or more component parts of the drive housing 408 used to activate the manual knife bailout system may include or otherwise be made of a magnetically responsive material. When such component parts are physically moved, a disturbance in the magnetic field may be detected, and that may provide a positive indication that the manual knife bailout system is being activated. In some embodiments, once the disturbance is detected, the user (i.e., a surgeon, a scrub nurse, etc.) may be informed of the status change and subsequently provided with instructions on how to complete the knife bailout procedure or otherwise instructions on how to reverse commencement of the knife bailout procedure.

Figure 8A:
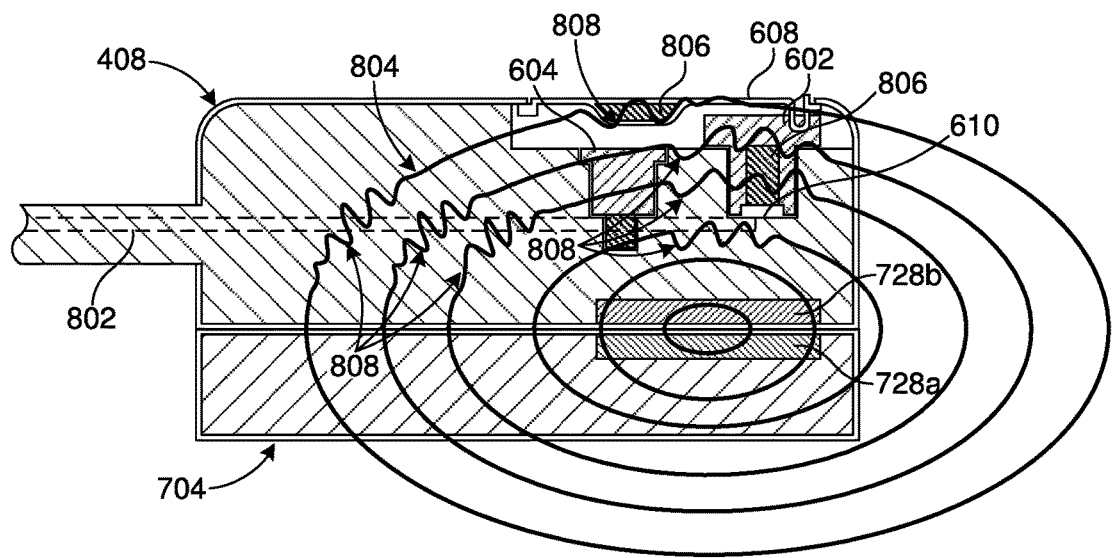
FIGS. 8A and 8B are cross-sectional side views of the drive housing of FIGS. 4 and 7 inductively coupled to the tool driver of FIG. 7, according to one or more embodiments.
Figure 8B:
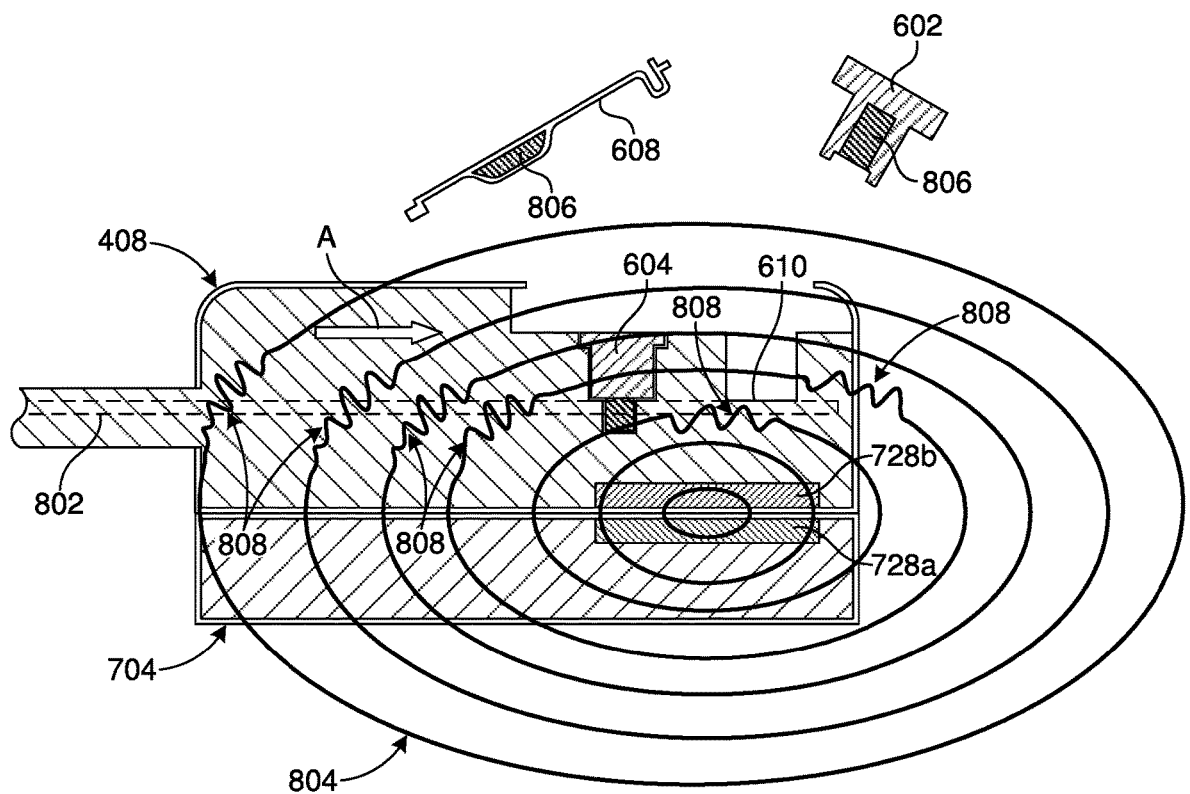

FIGS. 8A and 8B are cross-sectional side views of the drive housing 408 inductively coupled to the tool driver 704, according to one or more embodiments. FIGS. 8A-8B also depict various component parts of the manual knife bailout system, including the bailout tool 602 and the bailout cap 604. In the illustrated embodiment, the bailout tool 602 is stored within the drive housing 408 and seated (received) within the pocket 610. The user can access the bailout tool 602 by first removing the bailout panel 608. The bailout tool 602 can then be removed from the pocket 610 and mated to the bailout cap 604 to rotate the bailout cap 604 and thereby manually retract the knife (not shown). As mentioned above, rotating (driving) the bailout cap 604 in the first direction (e.g., counter-clockwise) will cause an interconnected firing rod 802 (shown in dashed lines) to retract proximally, as indicated by the arrow A in FIG. 8B. The knife may be operatively coupled to the distal end of the firing rod 802 at the end effector 404 (FIG. 4), and proximal movement of the firing rod 802 correspondingly retracts the knife in the proximal direction A.

Mounting the drive housing 408 to the tool driver 704 places the second inductor coil 728b of the drive housing 408 in proximity to the first inductor coil 728a of the tool driver 704. As controlled by the computer system 706 (FIG. 7, the first inductor coil 728a may be configured to generate (emit) a magnetic field 804 that propagates radially outward. As briefly described above, the magnetic field 804 may be received or otherwise sensed by the second inductor coil 728b to facilitate data transmission and electrical power transfer (i.e., voltage or current) to the circuitry of the internal computer 722 (FIG. 7).

In some embodiments, as illustrated, one or more component parts of the manual knife bailout system may be made of or otherwise include a magnetically responsive material 806 that causes field distortions 808 in the magnetic field 804. The magnetically responsive material 806 may comprise any magnetically responsive material capable of distorting or disrupting the magnetic field 804. The magnetically responsive material 806 may comprise, for example, a conductive metal such as, but not limited to, silver, copper, gold, aluminum, zinc, nickel, brass, bronze, a ferrous metal (e.g., iron, carbon steel, stainless steel, etc.), platinum, lead, any alloy thereof, or any combination thereof. The magnetically responsive material 806 may alternatively comprise a conductive polymer, graphite, carbon fibers, or any combination thereof.

In some embodiments, all or a portion of one or more of the bailout tool 602, the bailout panel 608, and the firing rod 802 may be made of the magnetically responsive material 806. In other embodiments, the magnetically responsive material 806 may be included with or otherwise attached to one or more of the bailout tool 602, the bailout panel 608, and the firing rod 802. The magnetically responsive materials 806 will distort the magnetic field 804 and generate field distortions 808 that may be measured or otherwise sensed by the second inductor coil 728b.

More specifically, the second inductor coil 728b may be configured to measure the electromotive force (i.e., a voltage or a current) generated within the second inductor coil 728b; i.e., how much electrical potential is resulting in the second inductor coil 728b due to the magnetic field 804. Because the electrical potential is driven by how much magnetic flux is driven through the second inductor coil 728b, the measured electrical potential can also serve as a measurement of the magnetic flux in the second inductor coil 728b. The magnetically responsive materials 806 will distort the magnetic flux of the magnetic field 804 depending on the position of the magnetically responsive materials 806 within the magnetic field 804. If the physical position of the magnetically responsive materials 806 changes, the magnetic flux of the magnetic field 804 will correspondingly change and the second inductor coil 728b will be able to detect the alteration and position change.

Referring to FIG. 8A, the component parts of the manual knife bailout system are properly stowed and otherwise in position for normal use of the surgical tool 400 (FIG. 4). When the drive housing 408 is first installed on the tool driver 704, the intensity of the magnetic field 804 and the resulting field distortions 808 generated by the magnetically responsive materials 806 included with the component parts of the manual knife bailout system may be measured and recorded. This data may be stored (logged) by the computer system 706 (FIG. 7) or the internal computer 722 (FIG. 7) to provide a normal operating state for the surgical tool 400, and any variation from this normal operating state may provide an indication that the manual knife bailout system has been activated or is about to be activated. Alternatively, the memory 224 of the internal computer 722 may already have stored therein known field distortions 808 generated in the magnetic field 804 when the drive housing 408 is coupled to the tool driver 704 and in the normal operating state. In such embodiments, the computer system 706 (FIG. 6) may interpret the measured magnetic field 804 and associated field distortions 808 and recognize the surgical tool 400 based on the measured magnetic field 804 and associated field distortions 808.

The intensity of the magnetic field 804 may then be continuously monitored and measured by one or both of the computer system 706 (FIG. 7) and the internal computer 722 (FIG. 7). In some embodiments, the real-time intensity of the magnetic field 804 may then be compared against the intensity corresponding to the normal operating state and one or more predetermined intensity thresholds. The predetermined intensity thresholds may correspond to a known magnetic field 804 and associated field distortion 808 resulting from a predetermined position (status) of the one or more component parts, which may might indicate when the manual knife bailout system of the surgical tool 400 (FIG. 4) has been activated or is about to be activated. The predetermined intensity thresholds that may be stored in the memory of the computer system 706 or the internal memory 724 (FIG. 7) of the internal computer 722. The predetermined position of the one or more component parts can include, but is not limited to, 1) the bailout tool 602 and the bailout panel 608 are present, 2) the bailout tool 602 is present but the bailout panel 608 is removed, 3) the bailout panel 608 is present but the bailout tool 602 is removed, 4) both the bailout tool 602 and the bailout panel 608 are removed, 5) the firing rod 802 is located in an extended position, and 6) the firing rod 802 is located in an retracted position.

In FIG. 8B, the bailout tool 602, the bailout panel 608, and the firing rod 802 have each been physically moved relative to the drive housing 408 and the magnetic field 804, and the field distortions 808 caused by the magnetically responsive material 806 corresponding to each component part has correspondingly changed. In the illustrated scenario, the bailout tool 602 and the bailout panel 608 have each been moved out of the range of the magnetic field 804, thus eliminating any field distortions 808 that might be attributable to the presence of the bailout tool 602 and the bailout panel 608. In such cases, the measured intensity of the magnetic field 804 will correspondingly change, which may provide a positive indication that the bailout tool 602 and the bailout panel 608 have each been removed from the drive housing 408. Moreover, in the illustrated scenario, the firing rod 802 has moved proximally A, which also alters the resulting field distortions 808 and the measured intensity of the magnetic field 804, which may provide a positive indication that the firing rod 802 has moved to the retracted position (state).

If the computer system 706 (FIG. 7) determines that the manual knife bailout system has been activated, the computer system 706 (FIG. 7) may be programmed and otherwise configured to notify the user (i.e., a surgeon, a scrub nurse, etc.) of the status change. In some embodiments, the notification may comprise a visual notification provided on the visual display 206 (FIG. 2), but in other embodiments the notification may be audible or tactile (i.e., felt through the user input devices held by the surgeon). In at least one embodiment, the notification may provide the user with instructions on how to successfully complete the manual knife bailout procedure or otherwise instructions on how to reverse commencement of the bailout procedure (e.g., instructions on how to replace the bailout tool 604 and/or the bailout panel 608).

If it is determined that one or more of the component parts of the manual knife bailout system is missing and otherwise outside of the range of the magnetic field 804, the computer system 706 (FIG. 7) may further be programmed and otherwise configured to send an alert or notice to ensure an accurate accounting for the missing objects. This may prove advantageous in avoiding potential loss of tool objects or parts in the patient.

While the preceding discussion mentions the bailout tool 602, the bailout panel 608, and the firing rod 802 as component parts of the manual knife bailout system that may affect the magnetic field 804, the manual knife bailout system may include additional component parts including, but not limited to various gears, racks, levers, etc. included within the drive housing 408. Accordingly, the present disclosure contemplates that any of the gears, racks, levers, etc. may be made of the magnetically responsive material 806, or alternatively, the magnetically responsive material 806 may be attached thereto and equally affect the magnetic field 804 to indicate activation of the manual knife bailout system. Moreover, the principles of the present disclosure are not limited to monitoring the manual knife bailout system, but may alternatively be applied to other mechanisms or devices included in the drive housing 408. In such embodiments, each mechanism or device may have its own predetermined intensity thresholds that will trigger tool-dependent responses when the magnetic field 804 is distorted.

Instead of measuring the intensity of the magnetic field 804 on the second inductor coil 728b to determine when the component parts of the manual knife bailout system are present or removed, it is also contemplated herein to measure the electromotive force (i.e., voltage or current) generated in the second inductor coil 728b. Alternatively, the phase delay of the magnetic field 804 may be measured to determine when the component parts of the manual knife bailout system are present or removed.

Figure 9:
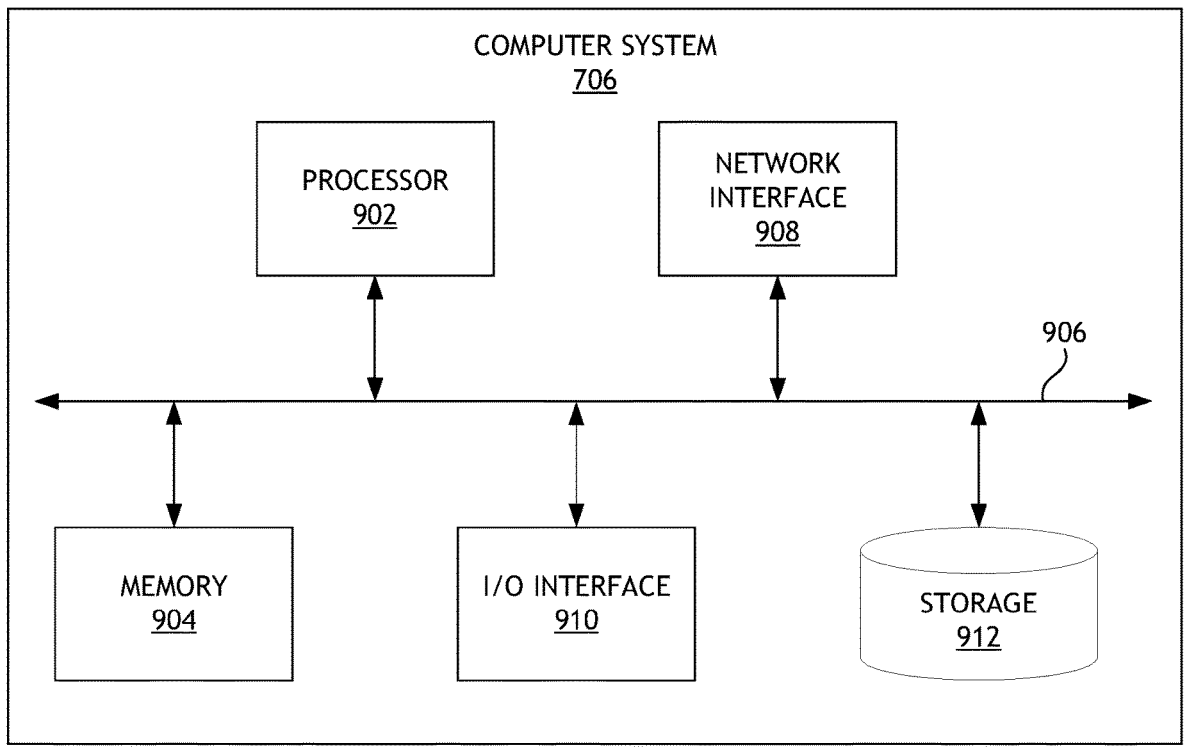
FIG. 9 illustrates an example embodiment of the computer system of FIG. 7.

FIG. 9 illustrates an example embodiment of the computer system 706 of FIG. 7. As shown, the computer system 706 includes one or more processors 902, which can control the operation of the computer system 706. "Processors" are also referred to herein as "controllers." The processor(s) 902 can include any type of microprocessor or central processing unit (CPU), including programmable general-purpose or special-purpose microprocessors and/or any one of a variety of proprietary or commercially available single or multi-processor systems. The computer system 706 can also include one or more memories 904, which can provide temporary storage for code to be executed by the processor(s) 902 or for data acquired from one or more users, storage devices, and/or databases. The memory 904 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 706 can be coupled to a bus system 906. The illustrated bus system 906 is an abstraction that represents any one or more separate physical busses, communication lines/interfaces, and/or multi-drop or point-to-point connections, connected by appropriate bridges, adapters, and/or controllers. The computer system 706 can also include one or more network interface(s) 908, one or more input/output (IO) interface(s) 910, and one or more storage device(s) 912.

The network interface(s) 908 can enable the computer system 706 to communicate with remote devices, e.g., other computer systems, over a network, and can be, for non-limiting example, remote desktop connection interfaces, Ethernet adapters, and/or other local area network (LAN) adapters. The IO interface(s) 910 can include one or more interface components to connect the computer system 706 with other electronic equipment. For non-limiting example, the IO interface(s) 910 can include high speed data ports, such as universal serial bus (USB) ports, 1394 ports, Wi-Fi, Bluetooth, etc. Additionally, the computer system 706 can be accessible to a human user, and thus the IO interface(s) 910 can include displays, speakers, keyboards, pointing devices, and/or various other video, audio, or alphanumeric interfaces. The storage device(s) 912 can include any conventional medium for storing data in a non-volatile and/or non-transient manner. The storage device(s) 912 can thus hold data and/or instructions in a persistent state, i.e., the value(s) are retained despite interruption of power to the computer system 706. The storage device(s) 912 can include one or more hard disk drives, flash drives, USB drives, optical drives, various media cards, diskettes, compact discs, and/or any combination thereof and can be directly connected to the computer system 706 or remotely connected thereto, such as over a network. In an exemplary embodiment, the storage device(s) 912 can include a tangible or non-transitory computer readable medium configured to store data, e.g., a hard disk drive, a flash drive, a USB drive, an optical drive, a media card, a diskette, a compact disc, etc.

The elements illustrated in FIG. 9 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 706 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 706 can also include a web server for generating and/or delivering the web pages to client computer systems.

In an exemplary embodiment, the computer system 706 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system 706 can also include any of a variety of other software and/or hardware components, including by way of non-limiting example, operating systems and database management systems. Although an exemplary computer system is depicted and described herein, it will be appreciated that this is for the sake of generality and convenience. In other embodiments, the computer system may differ in architecture and operation from that shown and described here.

Embodiments disclosed herein include:

A. A robotic surgical tool includes a tool driver in communication with a computer system, a drive housing mountable to the tool driver and including one or more component parts made of or including a magnetically responsive material, a first inductor coil included on the tool driver and configured to generate a magnetic field, a second inductor coil included on the drive housing and configured to measure an intensity of the magnetic field and a field distortion caused by the one or more component parts, wherein a change in the field distortion provides an indication of movement of the one or more component parts.

B. A method of operating a robotic surgical tool includes mounting a drive housing to a tool driver in communication with a computer system, the drive housing including one or more component parts made of or including a magnetically responsive material, inductively coupling the drive housing to the tool driver by generating a magnetic field with a first inductor coil included on the tool driver and sensing the magnetic field with a second inductor coil included on the drive housing, measuring an intensity of the magnetic field and a field distortion caused by the one or more component parts with the second inductor coil, and detecting a change in the field distortion with the second inductor coil and thereby providing an indication of movement of the one or more component parts.

C. A robotic surgical tool includes a tool driver in communication with a computer system, a drive housing mountable to the tool driver and including a manual knife bailout system that includes one or more component parts selected from the group consisting of a bailout tool, a bailout panel, and a firing rod, wherein at least one of the one or more component parts is made of or includes a magnetically responsive material, a first inductor coil included on the tool driver and configured to generate a magnetic field, a second inductor coil included on the drive housing and configured to measure an intensity of the magnetic field and a field distortion caused by the one or more component parts, wherein a change in the field distortion provides an indication of movement of at least one of the bailout tool, the bailout panel, and the firing rod.

Each of embodiments A, B, and C may have one or more of the following additional elements in any combination: Element 1: wherein the magnetically responsive material comprises a magnetically responsive material selected from the group consisting of conductive metal, a conductive polymer, graphite, carbon fibers, and any combination thereof. Element 2: wherein the drive housing further includes an internal computer in communication with the second inductor coil and programmed to process the intensity of the magnetic field and the change in the field distortion. Element 3: wherein the computer system is programmed to provide a notification when the change in the field distortion is detected. Element 4: wherein the notification comprises a visual notification provided on a visual display. Element 5: wherein the notification comprises an audible or tactile notification. Element 6: wherein the one or more component parts of the drive housing form part of a manual knife bailout system, and wherein the measuring the change in the field distortion provides an indication that the manual knife bailout system has been activated.

Element 7: wherein the drive housing further includes an internal computer in communication with the second inductor coil, the method further comprising processing the intensity of the magnetic field and the change in the field distortion with the internal computer. Element 8: further comprising providing a notification with the computer system when the change in the field distortion is detected. Element 9: further comprising providing a visual notification on a visual display in communication with the computer system. Element 10: wherein providing the notification comprises providing an audible or tactile notification. Element 11: wherein measuring the intensity of the magnetic field and the field distortion comprises measuring the intensity and the field distortion upon inductively coupling the drive housing to the tool driver. Element 12: wherein measuring the intensity of the magnetic field and the field distortion comprises measuring the intensity and the field distortion prior to inductively coupling the drive housing to the tool driver, and storing the intensity and the field distortion within a memory of an internal computer included in the drive housing. Element 13: wherein detecting the change in the field distortion comprises comparing the change in the field distortion with a predetermined intensity threshold corresponding to a known magnetic field and a known field distortion resulting from a predetermined position of the one or more component parts, and matching the change in the field distortion with the predetermined intensity threshold.

Element 14: wherein the magnetically responsive material comprises a magnetically responsive material selected from the group consisting of conductive metal, a conductive polymer, graphite, carbon fiber, and any combination thereof. Element 15: wherein the bailout tool is stored within the drive housing and accessible by removing the bailout panel. Element 16: wherein the drive housing further includes a bailout cap and the bailout tool is matable with the bailout cap, and wherein rotating the bailout tool correspondingly rotates the bailout cap, which causes the firing rod to translate longitudinally. Element 17: wherein the computer system is programmed to provide a notification when the change in the field distortion is detected.

By way of non-limiting example, exemplary combinations applicable to A, B, and C include: Element 3 with Element 4; Element 3 with Element 5; Element 8 with Element 9; and Element 8 with Element 10.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A robotic surgical tool, comprising:
    a tool driver;
    a drive housing inductively coupled to the tool driver when mounted to the tool driver and generating a magnetic field, the drive housing including one or more component parts made of or including a magnetically responsive material; and
    a computer system programmed to process an intensity of the magnetic field and a field distortion caused by the one or more component parts, and further programmed to generate a notification when the field distortion changes.

2. The robotic surgical system of claim 1, wherein the notification comprises a visual notification provided on a visual display.

3. The robotic surgical system of claim 2, wherein the visual notification comprises instructions on how to complete or reverse a bailout procedure.

4. The robotic surgical system of claim 1, wherein the notification comprises an audible or tactile notification.

5. The robotic surgical system of claim 1, further comprising:
    a transmitter mounted to one of the tool driver and the drive housing and configured to generate the magnetic field; and
    a receiver mounted to the other of the tool driver and the drive housing and configured to sense the intensity of the magnetic field and the field distortion.

6. The robotic surgical system of claim 5, wherein the transmitter comprises a first inductor coil, and the receiver comprises a second inductor coil.

7. The robotic surgical system of claim 1, wherein a change in the field distortion is an indication of movement of the one or more component parts.

8. The robotic surgical system of claim 1, wherein the one or more component parts of the drive housing form part of a manual knife bailout system, and wherein the field distortion changes when the manual knife bailout system has been activated.

9. A method of operating a robotic surgical tool, comprising:
    mounting a drive housing to a tool driver, the drive housing including one or more component parts made of or including a magnetically responsive material;
    inductively coupling the drive housing to the tool driver and generating a magnetic field and a field distortion caused by the one or more component parts;
    processing with a computer system an intensity of the magnetic field and the field distortion; and
    generating a notification with the computer system when the field distortion changes.

10. The method of claim 9, further comprising moving one of the one or more component parts and thereby generating a change in the field distortion.

11. The method of claim 9, wherein generating the notification comprises providing a visual notification on a visual display in communication with the computer system.

12. The method of claim 9, wherein generating the notification comprises providing an audible or tactile notification.

13. The method of claim 9, wherein processing the intensity of the magnetic field and the field distortion comprises:
    measuring the intensity and the field distortion prior to inductively coupling the drive housing to the tool driver; and
    storing the intensity and the field distortion within a memory of an internal computer included in the drive housing.

14. The method of claim 9, further comprising detecting a change in the field distortion by:
    comparing the change in the field distortion with a predetermined intensity threshold corresponding to a known magnetic field and a known field distortion resulting from a predetermined position of the one or more component parts; and
    matching the change in the field distortion with the predetermined intensity threshold.

15. A robotic surgical tool, comprising:
    a tool driver;
    a drive housing inductively coupled to the tool driver when mounted thereto and generating a magnetic field, the drive housing including a manual knife bailout system that includes one or more component parts selected from the group consisting of a bailout tool, a bailout panel, and a firing rod, wherein at least one of the one or more component parts is made of or includes a magnetically responsive material;
    a computer system programmed to process an intensity of the magnetic field and a field distortion caused by the one or more component parts, and further programmed to generate a notification when the field distortion changes.

16. The robotic surgical system of claim 15, wherein the notification comprises a visual notification provided on a visual display.

17. The robotic surgical system of claim 16, wherein the visual notification comprises instructions on how to complete or reverse a bailout procedure.

18. The robotic surgical system of claim 15, wherein the notification comprises an audible or tactile notification.

19. The robotic surgical system of claim 15, further comprising:
    a transmitter mounted to one of the tool driver and the drive housing and configured to generate the magnetic field; and
    a receiver mounted to the other of the tool driver and the drive housing and configured to sense the intensity of the magnetic field and the field distortion.

* * * * *